United States Patent [19]

Parkell et al.

[11] 4,019,372

[45] Apr. 26, 1977

[54] CHROMATOGRAPHIC DETECTOR SYSTEM

[75] Inventors: Erwin C. Parkell, Galena, Md.; John A. Stamm, Wilmington, Del.

[73] Assignee: E. I. DuPont de Nemours and Company, Wilmington, Del.

[22] Filed: Dec. 16, 1974

[21] Appl. No.: 534,092

Related U.S. Application Data

[63] Continuation-in-part of Ser. No. 470,635, May 16, 1974, abandoned.

[52] U.S. Cl. .................. 73/61.1 C; 210/198 C; 356/181
[51] Int. Cl.² .................................. G01N 31/08
[58] Field of Search ............. 73/61.1 C, 23.1; 356/246, 181; 250/573, 576; 210/24 C, 198 C

[56] References Cited
UNITED STATES PATENTS 3,522,725  8/1970  Waters ........................... 73/61.1 C
3,941,487  3/1976  Ehret et al. ................ 73/61.1 C X

*Primary Examiner*—Herbert Goldstein
*Assistant Examiner*—Joseph W. Roskos

[57] ABSTRACT

The present invention is a liquid chromatograph comprising a chromatographic column; means, including a pump, connected to the input of the column for injecting a sample under pressure into the column; and a detector system, including an optically transparent flow cell and a connecting means connecting the flow cell to the output of the column. The connecting means is in thermal contact or at least thermal equilibrium with the flow cell for a sufficient length so that any liquid passing through the connecting means comes to thermal equilibrium with the flow cell before entering the optically transparent flow cell.

5 Claims, 7 Drawing Figures

U.S. Patent  April 26, 1977  Sheet 1 of 4  4,019,372
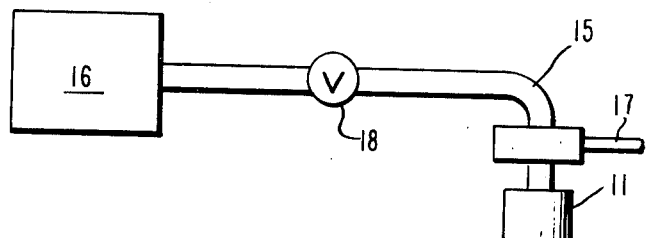
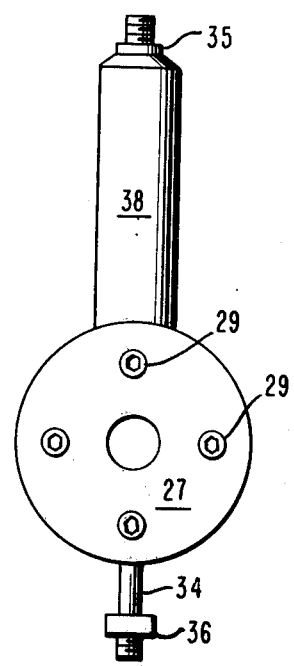
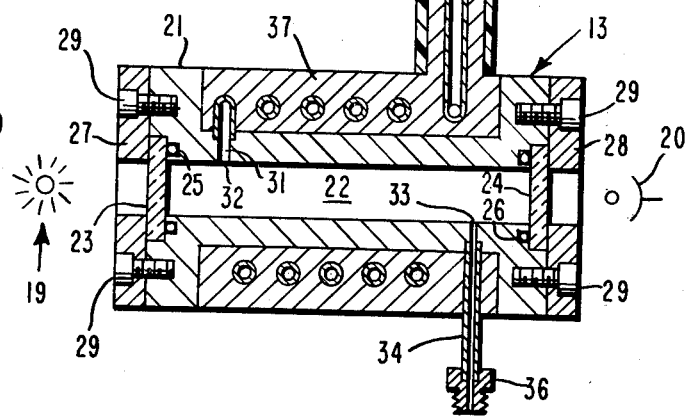
FIG. 1B
FIG. 1A
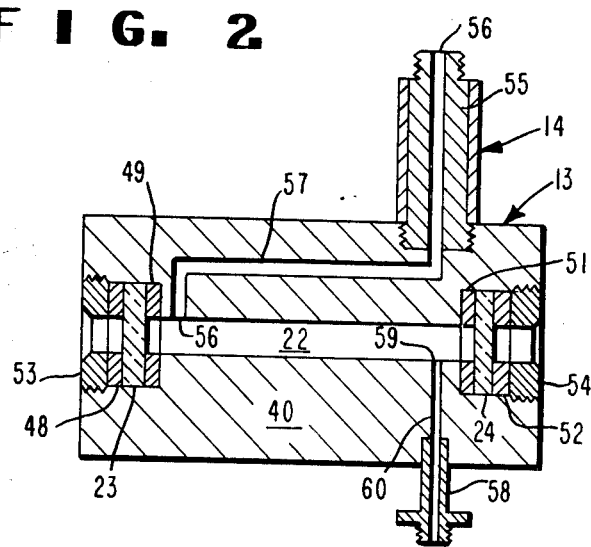
FIG. 2

CHROMATOGRAPHIC DETECTOR SYSTEM

CROSS REFERENCE TO RELATED APPLICATIONS

This application is a continuation-in-part of application Ser. No. 470,635 which filed on May 16, 1974 by the same inventors and now abandoned.

BACKGROUND OF THE INVENTION

This invention relates to the field of liquid chromatography. More specifically, it relates to the design and construction of an improved detection system for use in a liquid chromatograph, particularly a high pressure liquid chromatograph.

One of the most pervasive problems in liquid chromatography, particularly high pressure liquid chromatography, is noise produced in the output of the detector by the operation of the high pressure pump. In particular, when a reciprocating pump is used, the base line of the detector output contains a noise spectrum, usually in the form of a series of spikes corresponding to the cycles of the pump. While this noise is low level noise (generally considerably smaller than 0.01 absorbance units) it does limit the sensitivity of the instrument.

Various attempts have been made to eliminate the noise in the output of the detector caused by the pump. In particular, more expensive constant flow pumps have been used, or pulse damping systems have been incorporated into the liquid line. With the exception of the use of constant pressure pumps, none of the approaches that have been tried have been overly successful, and all require complication and costly additional components.

The detector used in a liquid chromatography is most often a photometer comprising a radiation source, a flow cell and a radiation detector. The effluent from the chromatographic column passes through the flow cell, which is optically transparent, and changes in the chemical composition of the effluent are measured by monitoring the change in its optical density, using the radiation source and the radiation detector to measure the change in light transmission.

In such a system, the radiation from the radiation source heats up the optical cell, and the liquid in it, above ambient temperature. It has been found that the pulses observed in the output of the detector are due to changes in the index of refraction of the liquid in the optical cell. The index of refraction of a liquid is dependent on its temperature. When the effluent from a chromatographic column enters the flow cell, it does so at ambient temperature. As it flows through the cell, its temperature is raised by contact with the flow cell and it leaves the flow cell at an elevated temperature. This does not cause a major problem in a constant flow system, because some equilibrium always exists between the temperature of the liquid entering the flow cell and the temperature of the liquid leaving the flow cell, and the photometer measures the mean or average index of refraction.

The situation is quite different when a reciprocating pump or some other periodic pumping means is used. In such a system, there is a periodic pulse of liquid entering the flow cell at ambient temperature. There is, therefore, a difference in the equilibrium index of refraction during the pulse and equilibrium index of refraction when the pulse stops. This difference appears in the output of the detector as noise, generally in the form of a spike.

There are a number of ways in which this particular problem can be solved. One way is to enclose the entire chromatographic system in an environment of controlled temperature, such as heat bath, which is maintained at a temperature equal to that of the flow cell. In this way, the liquid flowing through the chromatographic column and entering the flow cell would be at the same temperature as the liquid leaving the flow cell. Regardless of whether or not there were fluctuations in the flow of the fluid in the flow cell, the temperature of the liquid in the flow cell would be constant and the index of refraction of the liquid in the cell would also be constant.

Another way to achieve the same result is to monitor the temperature of the flow cell and the temperature of the effluent leaving the chromatographic column, and to actively control the temperature of the liquid leaving the chromatographic column until it is equal to the temperature of the flow cell.

Both of these techniques, however, are unduly complicated, and require expensive additional components. Applicant has found that the same result can be achieved by a simple, passive system.

SUMMARY OF THE INVENTION

The present invention is a liquid chromatograph comprising
  a. a chromatographic column;
  b. means, including a pump, connected to the input of the column for injecting a sample under pressure into the column; and
  c. a detector system, including an optically transparent flow cell, a source of radiation of irradiating the flow cell, a detector for measuring the intensity of the radiation from the source which passes through the flow cell, and connecting means connecting the flow cell to the output of the column, the connecting means being in thermal equilibrium with the flow cell for a sufficient length so that any liquid passing through the connecting means is in thermal equilibrium with the flow cell before entering the optically transparent portion of the flow cell.

In the preferred embodiment, the connecting means is in direct thermal contact with the thermal cell. In one embodiment, the connecting means can be a long narrow tube, partially coiled around the flow cell, encapsulated by and connected to the flow cell by a thermally conductive medium such as a polymer having metallic particles dispersed therein, a metal solder, or any other suitable thermally conductive medium.

In the second embodiment, the connecting means comprises internal channels formed within the flow cell.

BRIEF DESCRIPTION OF THE INVENTION

The present invention can most easily be described by reference to the following FIGURES in which:

FIG. 1A is a schematic illustration of a liquid chromatograph showing in a cross-sectional side view, one embodiment of the flow cell and connecting means of the present invention;

FIG. 1B is a full front view of the flow cell and connecting means of FIG. 1A;

FIG. 2 is a cross-sectional side view of another embodiment of the flow cell and connecting means of the present invention.

DETAILED DESCRIPTION OF THE INVENTION

Figure 3A:
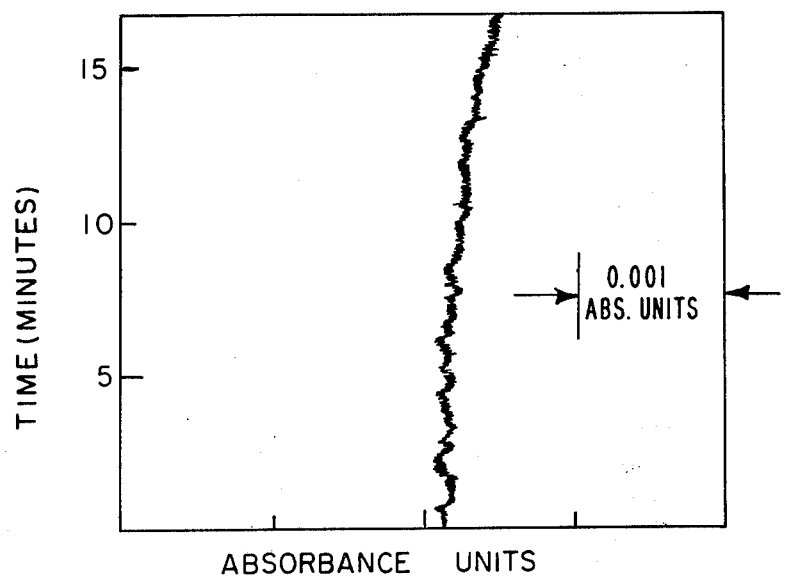
FIGS. 3A and 3B are graphs comparing the base line output of a detector in a liquid chromatograph utilizing the present invention with that of a liquid chromatograph without the present invention.

As shown in FIG. 1, a liquid chromatograph comprises a liquid chromatographic column 11 which usually contains some suitable packing material. The design and construction of such columns is well known to those skilled in the art, and suitable packing material can be purchased from a number of sources. One such packing material is composed of Zipax* surface porosity particles. The output of the chromatographic column 12 is connected to a flow cell, generally designated 13, by a connecting means, generally designated 14. The input of the column is connected via a tube 15 to a pump 16 which is used to pump carrier liquid to the column. Sample introduced into sample input 17 will be carried through the chromatographic colun by the carrier liquid. If the pump 16 is a reciprocating pump, a check valve 18 may be included in the input line to prevent backflow of the eluent supplied to the chromatographic column. *Registered trademark of the E. I. du Pont de Nemours & Co.

A detector used in liquid chromatography generally includes a radiation source 19 disposed on one side of the flow cell 13 and a radiation detector 20 disposed on the other side of the flow cell. Radiation from the radiation sources passes through the flow cell and the radiation detector detects changes in the intensity of the light passing through the flow cell caused by changes in the optical density of the medium in the flow cell. Any suitable flow cell design and construction well known to those skilled in the art can be used, and any suitable photometer system also well known to those skilled in the art can be used. Suitable components can be found, for example, in the Du Pont 841 Liquid Chromatograph.

The flow cell itself consists of a housing 21. Formed in this housing is a central channel 22. The cell may be made from any suitable material, preferably a metal such as stainless steel. Radiation transparent windows 23 and 24 are located on either end of channel 22. These windows may be made from any material suitably transparent to the radiation used in the analysis. Quartz or tempered glass windows are most often used. The windows are held in leak-tight association with housing 21 by some suitable means such as o-rings 25 and 26, which are disposed in annular recesses formed in the housing. The o-rings are compressed against windows 23 and 24 by end plates 27 and 28 which are held in place by screws 29. End plates 27 and 28 have apertures in them so light from the radiation source will reach internal channel 22. As illustrated, the arrangement provides an optical path for radiation from the radiation source to pass through the central channel 22 in flow cell 13 and impinge on radiation detector 20. Although the detector actually measures the optical density of the effluent, the output is sensitive to changes in the index of refraction of the effluent.

In the embodiment shown, housing 21 has a recessed channel or groove extending for nearly its entire length on the external surface of the housing between the flanges to which the end caps are connected. Connecting means are also provided to connect the output of the chromatographic column to the flow cell. In the embodiment illustrated, the connecting means is in the form of a long narrow tube, partially coiled about the flow cell in the region of the recessed channel. The coiled tube 30 terminates in a channel 31 opening into the central channel 22 of the flow cell through orifice 32. In the embodiment illustrated in FIG. 1, orifice 32 is located at one end of the central channel 22 in the flow cell, and a second orifice 33 is located at the other end of the central channel. This second orifice is connected to an output tube 34. Connector 35 is provided to connect tube 30 to an output of the liquid chromatographic column 12, and connector 36 is provided to connect the output of the flow cell to some suitable drain. In the embodiment illustrated, these connectors are indicated as screw fittings, but any suitable connected can be used.

Effluent from the chromatographic column passes through connecting tube 30, into central channel 22 through orifice 32 and out central channel 22 through orifice 33 into a suitable drain. The liqud in central channel 22 of the flow cell is located in the optical path between radiation source 19 and radiation detector 20.

Tube 30 which connects the chromatograpic column to the flow cell and is partially coiled about the flow cell, is encapsulated by a thermally conductive medium 37. Not only is the portion of the tube contained in the recess encapsulated by this thermally conductive medium, but also the extension of the tube leading from the coiled portion of the tube to the chromatographic column itself is encapsulated. The thermally conductive medium can be a polymer containing metallic particles dispersed therein, or a metal solder or any other suitable thermally conductive material. One suitable thermally conductive material is an epoxy containing silver particles sold under the tradename Tra-Duct 2902 by Tra-con, Inc. of Medford, Mass.

The purpose of the thermally conductive medium is to thermally connect the connecting means to the flow cell so that any liquid flowing through the connecting means will be brought into thermal equilibrium with the flow cell before entering the optically transparent internal channel 22 in the flow cell. The flow cell itself, is raised above ambient temperatures by the fact that it is being bombarded by radiation from radiation source 19. Fluid entering the connecting means and traveling through the coil in thermal equilibrium with the flow cell will reach thermal equilibrium with the temperature of the flow cell before entering the flow cell. Because of this, the liquid entering channel 22 in the flow cell is at a temperature equivalent to that of the liquid in channel 22, and there is no change in the index of refraction of the liquid in the flow cell due to the introduction of liquid at a different temperature.

To prevent cooling of the portion of the tube extending between the coiled region of the tube and the liquid chromatographic column by air currents, the upward extending portion of the encapsulated tube is further encapsulated by an insulating tube 38 which can be made from any suitable thermal insulating material such as Teflon fluorocarbon resin. Registered trademark of the E. I. du Pont de Nemours & Co.

There are two competing factors which must be considered in the design and construction of the flow cell and connecting means. The distance between the chromatographic column and orifice 32 through which the effluent from the chromatographic column is introduced into the central channel of the flow cell should be kept to a minimum. This is to eliminate "dead volume" and to increase the resolution of the instrument. For the practice of the present invention, however, the connecting means should be of sufficient length to allow the liquid passing through it to come to thermal equilibrium with the flow cell before the liquid enters channel 22 of the flow cell.

The length of the connecting means should be chosen with a number of factors in mind. Chief among these are the thermal conductives of the carrier and sample liquids, the material from which tubing 30 is made and encapsulating medium 37; and the rate at which the liquid is flowing through the system. If the flow rate through the system is low, and the thermal conductivity of the encapsulating medium is high, the liquid in tube 30 will come to thermal equilibrium with the flow cell after a short residence time in the connecting means. Therefore a reasonably short connecting means can be used. However, if the thermal conductivity of the encapsulating medium is low, and the flow through the system is high, then a longer connecting means must be used. In general, for preferred operation, the encapsulating medium should have a thermal conductivity greater than about $20 \times 10^{-4}$ gm cal-cm/cm$^2$/sec/°C., and the length of the channel in the connecting means should be at least 10.0 and preferably 15.0 centimeters long.

FIG. 2 shows a second embodiment of the flow cell 13 and connecting means 14 of the present invention in which at least a portion of the connecting means comprises an internal channel formed within the flow cell. In this embodiment, the flow cell housing 40 is formed from a single rod of some metal such as stainless steel and the central optical channel 22 is coaxially located in the rod. An expanded section of the central channel is located at each end of the central channel to house windows 23 and 24 whcih are held in place by gaskets 48, 49, 51 and 52 and by retaining rings 53 and 54 which threadedly engage the expanded section of channel 22.

Connecting means 14 is formed from a tube 55 which threadedly engages flow cell housing 40. The central channel 56 in tube 55 is connected to input orifice 56 of channel 22 by channel 57 which is formed within housing 40. Output tube 58 is connected to the output orifice 59 of channel 22 by channel 60. Channel 57 can be formed in housing 40 by any suitable means such as drilling, milling or casting, and it can take any desired shape such as a straight or spiral channel.

Figure 4:
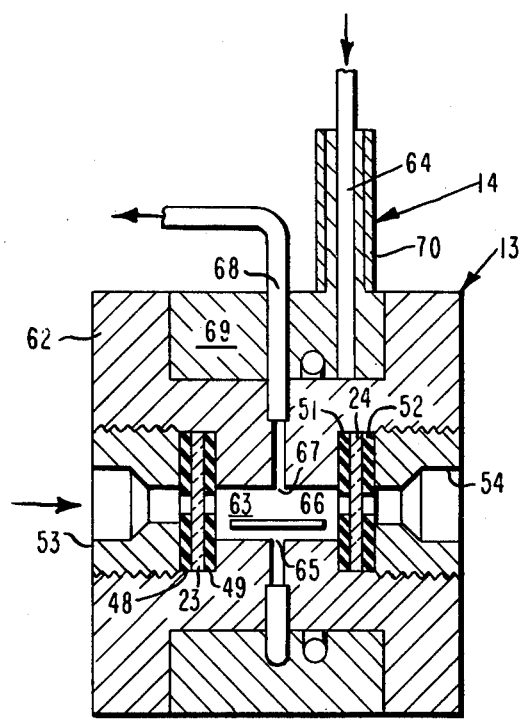
FIG. 4 is a cross-sectional side view of a third embodiment of the flow cell and connecting means of the present invention.

A third embodiment of the flow cell 13 and connecting means 14 of the present invention is shown in FIG. 4. In this embodiment, the flow cell is a split stream flow cell of the type disclosed in U.S. Pat. No. 3,614,452. Housing 62 has an I-shaped cross section with a central optical channel 63 formed in it. As shown in FIG. 2, the channel is sealed by windows 23 and 24 which are held in place by gaskets 48, 49, 51 and 52 and by retaining rings 53 and 54. The connecting means 13 is in the form of tube 64 coiled in the recess of housing 62 and connected to input orifice 65 in the central channel 63 of the flow cell. Upon entering the flow cell, the effluent from the chromatographic column is split into two streams by baffle 66 which recombine in the central channel 63 to flow out orifice 67 and tube 68. As shown in FIG. 1, the recess in housing 62 is filled with a thermally conductive medium 69 which also extends upward around the uncoiled portion of tube 64. Finally, the upward extending portion of the connecting means is insulated with a thermally insulating tube 70.

Figure 3B:
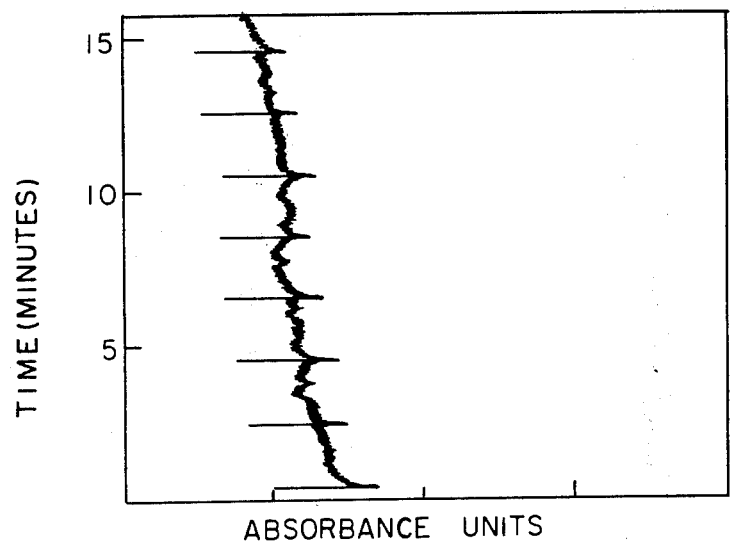

FIGS. 3A and 3B provide a comparison of the output of a chromatographic system utilizing the present invention (FIG. 3A) to that of a chromatographic system without the present invention (FIG. 3B). The chromatograph used was a Du Pont 841 Chromatograph utilizing a one meter Permaphase ODS column. The flow cell and connector system used was the one shown in FIG. 4. The flow cell itself was made from stainless steel, the windows from quartz and the gaskets from Teflon fluorocarbon resin. The connecting tube was a 15 centimeter stainless steel tube having an internal diameter of 0.01 inches. The thermally conductive medium encapsulating the connecting means was an oxide containing epoxy sold under the tradename Tra-Bond 2153 by Tra-Con, Inc. of Medford, Mass. The thermal conductivity of this medium was $24 \times 10^{-4}$ gm cal-cm/cm$^2$/sec/°C.

The path length of the optical cell was 10 millimeters and the volume of the optical cell was 8 microliters. The flow rate through both systems shown in FIGS. 3A and 3B was 1 ml./min. and the mobile phase consisted of 65% MeOH and 35% distilled $H_2O$. It can readily be seen from the graphs that the spikes shown in FIG. 3B are eliminated by the use of the present invention.

Figure 5:
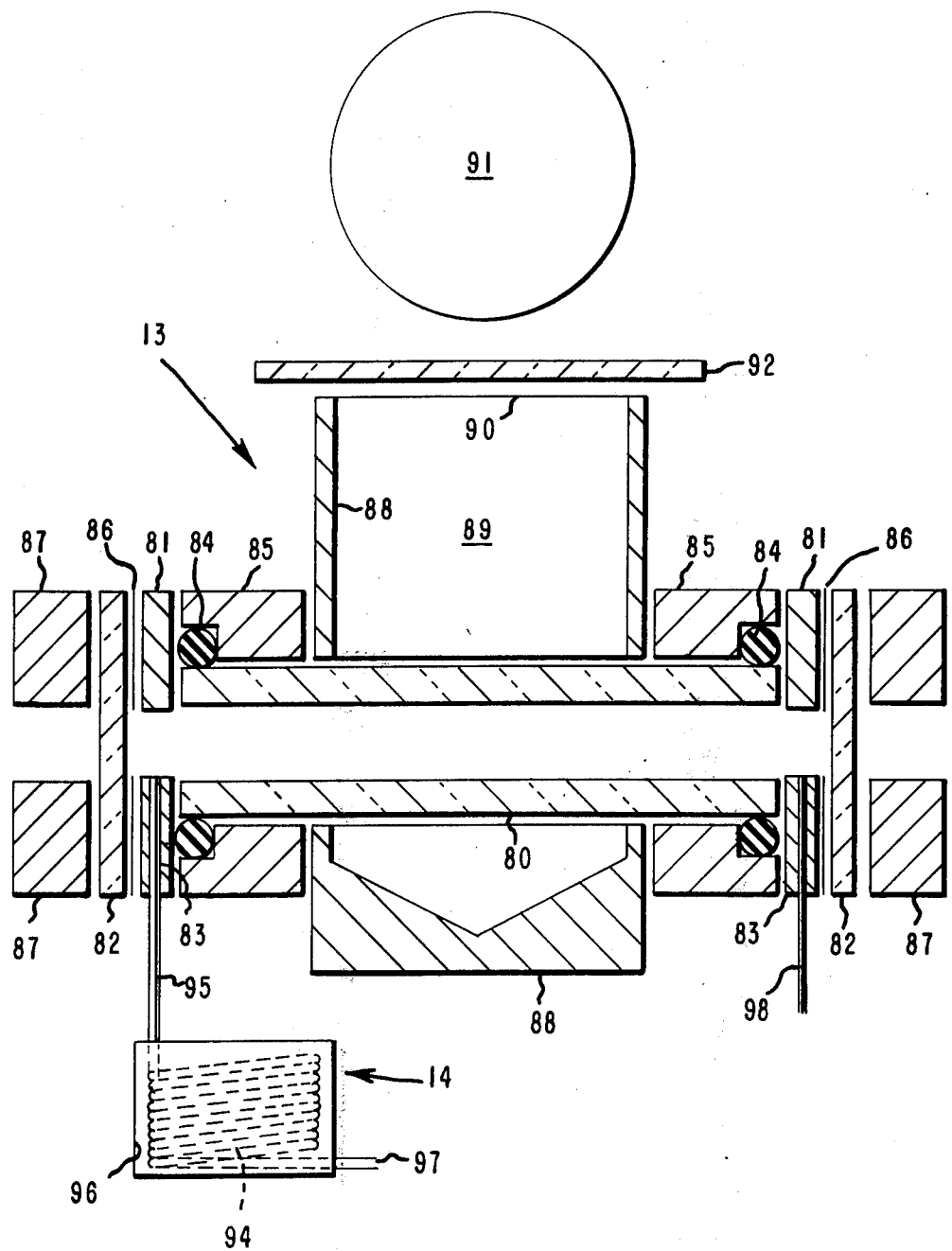
FIG. 5 is a cross-sectional view of a third embodiment of the flow cell and connecting means of the present invention.

A fourth embodiment of the flow cell 13 and connecting means 14 of the present invention is shown in FIG. 5. This FIGURE shows the present invention used with the dual purpose detector for a liquid chromatograph which permits simultaneous measurement of the optical absorbance and fluorescence of the effluent from a liquid chromatographic column. In this embodiment, the flow cell comprises a quartz tube 80, two flow rings 81 located on either end of tube 80, and two quartz windows 82 located at the ends of tube 80 outside flow rings 81. Each flow ring contains a narrow inlet 83, through which effluent from the chromatographic column enters or leaves the flow cell. The liquid effluent is contained in the flow cell by o-ring seals 84, located in an annular recess in flange 85, and by seals 86 located between the flow rings and the quartz windows. The entire structure is compressed by a flange 87 and is held in place by bolts, not shown. The aperture in the flow rings 87 should have a diameter slightly less than the internal diameter of the quartz tube.

Light from a light source, not shown, enters flow tube 80 through one of the quartz windows and passes through the cell out of the other quartz window to a detector, not shown. The detector system in the present embodiment also includes a reflective housing 88 which surrounds the quartz tube and, in conjunction with the walls of the tube, defines a fluorescence chamber 89. The reflective housing has an aperture 90 at the end located away from the tube, and a photomultiplier 91 disposed adjacent to that aperture. An emission filter 92 may be placed between the aperture and the photomultiplier so that only radiation of the desired light wavelength will reach the photomultiplier. Finally, flanges 85 act as scattering baffles which are used to block the light which is scattered at the end of flow tube and the windows from entering the fluorescence chamber. These baffles should be about twice the outer diameter of the flow tube in length.

The connecting means of the present invention comprises a heat exchanger 94 and a connecting tube 95. The heat exchanger actually comprises a coiled extension of tube 95. The coil is encapsulated by a suitable encapsulating medium 96 which can also encapsulate and connect tube 95 to the flow cell. The dimensions of the coil and the connecting tube are commensurate with those discussed above. In the embodiment shown, the heat exchanger of the connecting means is physically separate from the housing of the flow cell but located in the same temperature environment as the flow cel so that it is in thermal equilibrium with the flow cell. If the design of the flow cell permits, the heat exchanger can be connected to the flow cell so that there is direct thermal contact between the two, and the tube can be coiled about the flow cell as shown in FIG. 1. Sample from the liquid chromatographic column enters port 97, flows through coil 94 and into the flow cell through tube 95 and inlet 83. It flows out of the flow cell through inlet 83 and tube 98 located at the other end of the flow cell.

The description set forth above is for the purpose of illustrating the invention and is not intended to limit the scope of the invention set forth in the appended claims. In particular, it should be noted that the internal channel 50 formed in the housing of the flow cell can be of any form which can be conveniently constructed; the only criterion being that good thermal equilibrium is maintained between the connecting means and the flow cell itself.

What is claimed is:
1. A detector system for use with a liquid chromatographic column comprising an optically transparent flow cell and a connecting means connecting said flow cell to the output of said column, said connecting means being a long narrow tube, partially coiled around said flow cell and encapsulated by and connected to said flow cell by a thermally conductive medium, said connecting means being in thermal contact with said flow cell for a sufficient length so that any liquid passing through said connecting means come into thermal equilibrium with said flow cell before entering the optical transparent portion of said flow cell.

2. The detector of claim 1 wherein said thermally conductive medium is a polymer having metallic particles dispersed therein.

3. The detector of claim 1 wherein said thermal conductive medium is a metal solder.

4. The detector of claim 1 wherein the uncoiled, encapsulated portion of said connecting means is contained within an insulating sleeve.

5. A detector system for use with a liquid chromatographic column comprising an optically transpatent flow cell and a connecting means connecting said flow cell to the output of said column, at east a portion of said connecting means comprising internal channels formed within said flow cell, said connecting means being in thermal contact with said flow cell for a sufficient length so that any liquid passing through said connecting means comes into thermal equilibrium with said flow cell before entering the optical transparent portion of said flow cell.

* * * * *

Disclaimer

4,019,372.—*Erwin C. Parkell*, Galena, Md., and *John A. Stamm*, Wilmington, Del. CHROMATOGRAPHIC DETECTOR SYSTEM. Patent dated Apr. 26, 1977. Disclaimer filed Aug. 21, 1978, by the assignee, *E. I. du Pont de Nemours and Company*.

Hereby enters this disclaimer to all claims of said patent.

[*Official Gazette October 3, 1978.*]